(12) United States Patent
Callens et al.

(10) Patent No.: US 7,528,228 B2
(45) Date of Patent: May 5, 2009

(54) METHOD FOR SYNTHESIZING PEPTIDES COMPRISING AT LEAST ONE GLYCINE MOLECULE

(75) Inventors: Roland Callens, Grimbergen (BE); Frank Becu, Zwevezele-Wingene (BE); Frans Borremans, Destelbergen (BE)

(73) Assignee: Solvay S.A. (BE)

( * ) Notice: Subject to any disclaimer, the term of this patent is extended or adjusted under 35 U.S.C. 154(b) by 266 days.

(21) Appl. No.: 10/677,215

(22) Filed: Oct. 2, 2003

(65) Prior Publication Data

US 2004/0077830 A1 Apr. 22, 2004

(30) Foreign Application Priority Data

Oct. 4, 2002 (FR) ................................. 02 12493

(51) Int. Cl.
*C07K 2/00* (2006.01)
*A61K 38/00* (2006.01)
*A61K 38/07* (2006.01)

(52) U.S. Cl. ............................ 530/333; 514/2; 514/18; 530/300; 530/330

(58) Field of Classification Search ....................... None
See application file for complete search history.

(56) References Cited

U.S. PATENT DOCUMENTS

| 4,725,645 | A | 2/1988 | Anteunis et al. |
| 5,716,596 | A | 2/1998 | Dean et al. ................. 424/1.69 |
| 6,197,998 | B1 * | 3/2001 | Mimura et al. ............... 562/444 |

FOREIGN PATENT DOCUMENTS

| CH | 640 511 | 1/1984 |
| CH | 0640511 | 1/1984 |
| EP | 0184243 | 6/1986 |
| EP | 678501 A1 * | 10/1995 |
| EP | 0 950 664 | 10/1999 |

OTHER PUBLICATIONS

C. Marinzi, et al. Bioorg. Med. Chem. (2001) 9, pp. 2323-2328.*
U.K. Saha and R. Roy. Tetrahedron Letters (1995) 36(21), pp. 3635-3638.*
R.N. Zuckerman, et al. J. Am. Chem. Soc. (1992) 114, pp. 10646-10647.*
L.E. canne, et al. J. Am. Chem. Soc. (1996) 118, pp. 5891-5896.*
R.J. Simon, et al. Proc. Natl. Acad. Sci, USA (1992) 89, pp. 9367-9371.*
"Ullmann's Encyc. of Ind. Chemistry," 5th Ed., vol. B4, "Principles of Chemical Reaction Engineering and Plant Design," Eds. Elvers, B., et al (1992), pp. 387-388.
Masayasu Akiyama, et al, "Artificial Siderophores as a Model for Ferrichrome . . . ," Chemistry Letters 1995:225-226, XP-002961802 (1995).
McKendrick, J. E., et al, "Rapid mass spectrometric determination of preferred irreversible proteinase inhibitors in combinatorial libraries," Int'l J. of Mass Spectrometry 176:113-124 (1998).
Smales, C.M., et al, "A Novel Target Synthesis Laboratory for Students," J. of Chem. Education 76:1558-1560 (1999).
Myung-Gi Baek, et al, "Simultaneous Binding of Mouse Monoclonal Antibody and Streptavidin to Heterobifunctional Dendritic L-Lysine Core Bearing T-###Antigin Tumor Marker and Biotin," Bioorganic & Medicinal Chemistry 9:3005-3011, XP-002243804 (2001).
King, H. D., et al, "Facile synthesis of maleimide bifunctional linkers," Tetrahedron Letters 43:1987-1990 (2002).

* cited by examiner

*Primary Examiner*—Andrew D Kosar
(74) *Attorney, Agent, or Firm*—Connolly Bove Lodge & Hutz LLP

(57) ABSTRACT

Method for preparing a peptide or a peptide derivative comprising at least 2 enantiopure amino acids and at least one glycine molecule, comprising the reaction of a compound of general formula $XCH_2$—C(=O)—HN-A-COOY (II) with a compound of general formula $HNR^1R^2$ (III).

16 Claims, No Drawings

METHOD FOR SYNTHESIZING PEPTIDES COMPRISING AT LEAST ONE GLYCINE MOLECULE

The present invention relates to a method for synthesizing peptides or peptide derivatives comprising at least one glycine molecule, to some peptides or peptide derivatives and to some intermediates which can be used in the method of synthesis, and to their production.

The peptides or peptide derivatives comprising at least one glycine molecule are of use, for example, as medicinal products, as intermediates for producing peptides and as a spacer arm in pharmaceutical compositions intended to take biologically active principles specifically to certain cells of the body. A specific example of such a peptide is Gly-Phe-Leu-Gly (SEQ ID NO:1. In the state of the art (J. Chem. Educ, 1999, p. 1558-60) it is illustrated that the synthesis of this tetrapeptide starting from readily accessible products such as amino acids requires many protection, deprotection and coupling operations. The object of the invention is in particular to provide an efficient and economical method for synthesizing this peptide.

Patent Application EP-A-0950664 describes the production of N-glycyl-L-tyrosine by reacting N-chloroacetyl-L-tyrosine in the presence of ammonium ions.

It was desirable to make available a method for economically obtaining peptides or peptide derivatives, comprising glycine, more complex than in the state of the art and exhibiting a high purity, in particular optical purity.

Consequently, the invention relates to a method for preparing a peptide or a peptide derivative comprising at least two enantiopure amino acids and at least one glycine molecule, comprising the production of a peptide of general formula

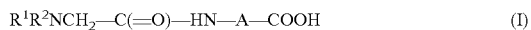  (I)

in which A denotes a peptide chain comprising at least two enantiopure amino acids; and $R^1$ and $R^2$ are chosen, independently, from H or alkyl, alkenyl and aryl which are optionally functionalized, a peptide and a nucleic acid, or $R^1$ and $R^2$ together form a cycloalkyl or cycloheteroalkyl substituent, by reacting a compound of general formula

  (II)

in which X denotes a group which can be substituted by nucleophilic substitution, chosen in particular from Cl and Br, and Y is chosen from H and cations, A denotes a peptide chain comprising at least two enantiopure amino acids; with a compound of general formula

  (III)

in which $R^1$ and $R^2$ are, independently, substituents chosen generally from H or alkyl, alkenyl and aryl which are optionally functionalized, a peptide and a nucleic acid, or $R^1$ and $R^2$ together form an optionally functionalized cyclic substituent.

It has been found, surprisingly, that the method according to the invention makes it possible to obtain, with a high preparative yield; complex peptides exhibiting several stereogenic centres, while at the same time avoiding racemization.

The peptides and peptide derivatives obtained in the method according to the invention generally exhibit a diastereomeric purity, defined as desired diastereomer weight content, of greater than or equal to 98%. Often, the diastereomeric purity is greater than or equal to 99%. Preferably the diastereomeric purity is greater than or equal to 99.5%. Particularly preferably, the diastereomeric purity is greater than or equal to 99.9%.

In the formulae describing the products used or obtained in the method according to the invention, A denotes a peptide chain comprising at least two enantiopure amino acids.

For the purposes of the present invention, the term "amino acid" is intended to denote any compound comprising at least one NR1R2 group, preferably $NH_2$ group, and at least one carboxyl group.

The enantiopure amino acids used in the present invention are chiral amino acids containing at least one asymmetric carbon.

The term "enantiopure amino acid" is intended to denote a chiral amino acid consisting essentially of an enantiomer. The enantiomeric excess (ee) is defined as: $ee(\%)=100(x_1-x_2)/(x_1+x_2)$, with $x_1>x_2$; $x_1$ and $x_2$ represent the content in the mixture of enantiomer 1 or 2 respectively.

An enantiopure amino acid the enantiomeric excess of which is greater than or equal to 99% is generally used. An enantiopure amino acid the enantiomeric excess of which is greater than or equal to 99.5% is preferred. Particularly preferably, an enantiopure amino acid the enantiomeric excess of which is greater than or equal to 99.9% is used.

Any chiral amino acid of natural or synthetic origin may be used.

Examples of enantiopure amino acids are, for example, the following natural amino acids:

alanine, valine, norvaline, leucine, norleucine, isoleucine, serine, isoserine, homoserine, threonine, allothreonine, methionine, ethionine, glutamic acid, aspartic acid, asparagine, cysteine, cystine, phenylalanine, tyrosine, tryptophan, lysine, arginine, histidine, ornithine, glutamine and citrulline.

Non-natural enantiomers can also be used.

Examples of enantiopure amino acids of synthetic origin which can be used as a basis of the reagent according to the invention comprising, for example, the following amino acids: (1-naphthyl)alanine, (2-naphthyl)alanine, homophenylalanine, (4-chlorophenyl)alanine, (4-fluorophenyl)alanine, (3-pyridyl)alanine, phenylglycine, diaminopimelic acid (2,6-diaminoheptane-1,7-dioc acid), 2-aminobutyric acid, 2-aminotetraline-2-carboxylic acid, erythro-β-methlphenylalanine, threo-β-methylphenylalanine, (2-methoxyphenyl)alanine, 1-amino-5-hydroxyindane-2-carboxylic acid, 2-aminoheptane-1,7-dioic acid, (2,6-dimethyl-4-hydroxyphenyl)alanine, erythro-β-methyltyrosine, threo-β-methyltyrosine.

The enantiopure amino acid is preferably selected from the amino acids of natural or synthetic origin named above.

The term "peptide chain" is preferably intended to denote a molecule combining at least two amino acids via a peptide bond. Peptide chains in which all the amino acids are combined via peptide bonds are particularly preferred. However, the term "peptide chain" can also denote peptide derivatives in which, for example, two or more amino acids are combined via another group, such as, for example, a ureido or thioureido group.

The peptide chain comprises at least 2 amino acids. Preferably, the number of amino acids in the peptide chain is greater than or equal to 3.

In another preferred variant, the number of amino acids in the peptide chain is greater than or equal to 4.

The number of amino acids that the peptide chain may comprise is not in principle limited. However, the peptide chain often comprises at most 100 amino acids. Preferably, the number of amino acids in the peptide chain is less than or equal to 20. Particularly preferably, the number of amino acids in the peptide chain is less than or equal to 15. It has been found that the method according to the invention is particularly suitable for the preparative production, via chemical process, of peptides and peptide derivatives exhibiting a high degree of diastereomeric purity.

Preferably, A denotes a peptide chain made up of a number of amino acids as described above.

The peptide chain comprises at least two enantiopure amino acids. Depending on the length of the peptide chain, the number of enantiopure amino acids in the peptide chain may be greater than or equal to 3. This number may also be greater than or equal to 4.

The peptide chain may consist of enantiopure amino acids. However, the peptide chain frequently comprises non-chiral amino acids such as, in particular, glycine. It has been found that the method according to the invention makes it possible to obtain peptides and peptide derivatives exhibiting a high degree of diastereomeric purity despite the presence of many stereogenic centres in the peptide chain, bringing about a risk of racemization.

Specific examples of peptide chains which can be used as group A in the method according to the invention correspond to the following sequences: Phe-Leu-Gly, Gly-Phe-Gly -Phe (SEQ ID NO: 2), Gly-Phe-Gly-Leu (SEQ ID NO: 3), Gly-Phe-Gly-Phe-Leu (SEQ ID NO: 4) and Gly-Phe-Leu-Gly-Phe-Leu (SEQ ID NO: 5). Phe-Leu-Gly is particularly preferable as a sequence.

In the compound of general formula (II), X denotes a group which can be substituted by nucleophilic substitution. Preferably, X denotes a group which can be substituted by nucleophilic substitution with a compound of general formula (III), in particular under the reaction conditions given in detail below. Specific examples of substituents X are chosen from —O— ester and halogen.

Esters within the group X are often chosen from fluorinated esters, such as fluoroacetates, fluoroalkyl sulphonates or alkyl- or arylsulphonates. Preferably, the esters are chosen from trifluoroacetate and trifluoromethanesulphonate and p-tolylsulphonate.

A halogen is very suitable as a group X. Among the halogens, chlorine and bromine are preferred. Chlorine is most particularly preferred.

In the compound of general formula (II), Y denotes a group chosen from H and cations. Among the suitable cations, mention may in particular be made of $Li^+$, $Na^+$, $K^+$, $Cs^+$, $Mg^{2+}$, $Ca^{2+}$, $Sr^{2+}$ and $Ba^{2+}$. In a preferred variant, y denotes a cation of formula $H_2NR^1R^{2+}$ which can be obtained by protonation of the compounds of general formula (III) described below. A group Y chosen from H and $NH_4^+$ is particularly preferred. It is understood that a given group Y can be exchanged for another in the course of implementing the method according to the invention.

The invention also relates to the compounds of general formula (II).

In the method according to the invention, the reaction is generally carried out at a temperature of greater than or equal to $-30°$ C. Often, the reaction is carried out at a temperature greater than or equal to $0°$ C. Preferably, the temperature is greater than or equal to $+10°$ C. In the method according to the invention, the reaction is generally carried out at a temperature of less than or equal to $+60°$ C. Often, the reaction is carried out at a temperature of less than or equal to $+50°$ C. Preferably, the temperature is less than or equal to $40°$ C.

In the method according to the invention, the reaction is generally carried out in a liquid medium. In this case, the pressure is chosen so as to maintain the reaction medium in the liquid state. Atmospheric pressure (approximately 101.3 kPa) and superatmospheric pressures are very suitable.

In the method according to the invention, aqueous ammonia is most particularly preferred as a compound of general formula (III).

When, in the compound of general formula (III), the substituent R1 and/or R2 is alkyl, it is often chosen from an alkyl group comprising from 1 to 20 carbon atoms. Specific examples of such groups are methyl, ethyl, n-propyl, isopropyl, n-butyl, isobutyl, tert-butyl, pentyl, cyclopentyl, cyclohexyl and benzyl. A methyl or ethyl group is preferred.

When, in the compound of general formula (m), the substituent R1 and/or R2 is alkenyl, it is often chosen from an alkenyl group comprising from 2 to 20 carbon atoms. Specific examples of such groups are 2-allyl, n-but-2-enyl, isobutenyl, cyclopentenyl and cyclohexenyl. An allyl group is preferred.

When, in the compound of general formula (III), the substituent R1 and/or R2 is aryl, it is often chosen from. an aryl group comprising from 6 to 24 carbon atoms. Specific examples of such groups are phenyl, 1-tolyl, 2-tolyl, 3-tolyl, xylyl, 1-naphthyl and 2-naphthyl. A phenyl or tolyl group is preferred.

When, in the compound of general formula (III), the substituents R1 and R2 together form a cyclic substituent, the heterocycle including the NH group is generally a ring made up of 3, 4, 5, 6 or 7 atoms. Specific examples of such heterocycles are pyrrolidine, piperidine, morpholine, 1,2,3,4-tetrahydroquinoline, 1,2,3,4-tetrahydroisoquinoline, perhydroquinoline, perhydroisoquinoline and (1H)-indole. Pyrrolidine, piperidine and morpholine are preferred.

When, in the compound of general formula (III), the substituent R1 and/or R2 is a peptide, this peptide comprises at least two amino acids. Often, the peptide comprises at least three amino acids. In a preferred aspect, the peptide comprises at least four amino acids. When, in the compound of general formula (III), the substituent R1 and/or R2 is a peptide, the number of amino acids which it comprises is not in principle limited. However, the peptide often comprises at most 100 amino acids. In a preferred aspect, the peptide comprises at most 20 amino acids.

In one variant, the compound of general formula (III) is a compound of general formula (I) as described above, in which at least one substituent R1 or R2 is H. Preferably R1 and R2 are H. When, in this variant, A is identical in the compound of general formula (II) and the compound of general formula (III), the product obtained is a peptide derivative of general formula

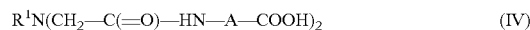

$$R^1N(CH_2—C(=O)—HN—A—COOH)_2 \quad (IV)$$

in which A is a peptide chain, preferably as defined above, and $R^1$ is as defined above.

When, in this variant, A is not identical in the compound of general formula (II) and the compound of general formula (III), the product obtained is a peptide derivative of general formula

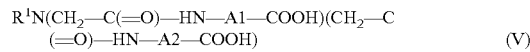

$$R^1N(CH_2—C(=O)—HN—A1—COOH)(CH_2—C(=O)—HN—A2—COOH) \quad (V)$$

in which A1 and A2 denote different peptide chains, preferably corresponding to the definition of substituent A given above, and $R^1$ is as defined above.

The invention also relates to peptide derivatives of general formula (IV) and (V).

Preferred peptide derivatives of general formula (IV) or (V) are those in which A denotes a peptide chain made up of 2 to 20 amino acids, comprising at least two enantiopure amino acids.

These peptide derivatives can be used as constituents in pharmaceutical compositions, for example as a spacer arm in pharmaceutical compositions intended to take biologically active principles specifically to certain cells of the body.

The invention consequently also relates to a pharmaceutical composition comprising the peptide derivatives of general formula (IV) or (V). Preferably, the pharmaceutical compositions comprise the peptide derivatives of general formula (IV) or (V) as a spacer arm. The derivatives in which A or A1 and/or A2 is chosen from Phe-Leu and Phe-Leu-Gly are preferred.

The pharmaceutical compositions can be prepared, for example, by a method comprising
(a) derivatization of the central NH group of a peptide derivative of general formula (IV) and (V) in which R1 is H, with a polymerizable group such as a methacrolyl group, optionally after protection of other functional groups of the peptide, such as the terminal carboxyl group(s);
(b) copolymerization of the derivatized peptide derivative with a suitable comonomer, such as, for example, a functionalized methacrylamide, in particular N-(2-hydroxypropyl)methacrylamide;
(c) optionally, deprotection of the terminal carboxyl group(s);
(d) condensation of the medicinal product, for example daunomycin, with the optionally protected carboxyl group.

In a first variant of the method according to the invention, the reaction is generally carried out in a liquid medium containing at least 25% by weight, relative to the total weight of the liquid medium, of compound of general formula (III). More commonly, the liquid medium contains at least 30% by weight of compound of general formula (III). The upper limit of the content of compound of general formula (III) corresponds in principle to the limit of solubility of the compound of general formula (III) in the chosen medium.

In a second variant, the reaction is carried out in a liquid medium in which a concentration of the compound of general formula (III) of less than or equal to 10% by weight, relative to the total weight of the liquid medium, is maintained. A concentration of the compound of general formula (II) of less than or equal to 5% by weight is preferred. A concentration of the compound of general formula (II) of less than or equal to 2% by weight is more particularly preferred. A concentration of the compound of general formula (II) of less than or equal to 1% is most particularly preferred. Generally, the reaction is carried out in a liquid medium in which concentration of the compound of general formula (II) of greater than or equal to 0.001% by weight, relative to the total weight of the liquid medium, is maintained. Often, the concentration of the compound of general formula (II) is greater than or equal to 0.01% by weight.

In the second variant, an advantageous way to maintain the desired concentration of compound of general formula (II) comprises adding the compound of general formula (II) to the liquid medium gradually.

The gradual addition of the compound of general formula (II) may, for example, be an addition carried out in several portions, which may or may not be identical. This method of adding the compound of general formula (II) corresponds to what is referred to, for bioreactors, as a "fed-batch" reaction (Ullmann's Encyclopedia of Industrial Chemistry, 5th Ed. Vol B4p. 387-388). Generally, a portion of compound of general formula (II) is introduced into the initial reaction medium, and then at least one other portion is subsequently added, during the reaction. The number of portions to be used is not theoretically limited, then becoming increasingly similar to another method of addition of the compound of general formula (II) according to which the gradual addition is carried out continuously.

However, a number of portions of at most 100 is generally used. Commonly, the number is at most 50. Most commonly, the number is at most 20. A number of at most 10 gives good results. A number of at most 5 is advantageous. A number of at most 4 is preferred. Excellent results are obtained with a number 2 or 3.

The time intervals between the additions of the portions are generally at least 1 min. Commonly, the intervals are at least 5 min. More commonly, the intervals are at least 30 min. Preferably, the intervals are at least 1 h. Intervals of approximately 2, 3, 4, 5 or 6 h give good results.

In another method of addition of the compound of general formula (II) in the method according to the invention, the gradual addition of at least one portion of the compound of general formula (II) is carried out continuously. This method of addition corresponds to what is referred to, for bioreactors, as an "extended fed-batch" reaction(Ullman's Encyclopedia of Industrial Chemistry, 5th Ed. Vol B4p. 387-388). It is possible, for example, to introduce a portion of compound of general formula (II) into the initial reaction medium, and then to subsequently add, during the reaction, a desired amount of compound of general formula (II) continuously, regulating the flow rate so as to maintain the concentration of the compound of general formula (II) below the desired concentration.

The second variant is particularly suitable when it is desired to prevent the subsequent reaction of the compound of general formula (I) with compound of general formula (II) present in the reaction medium.

The second variant is also equally suitable for carrying out a selective 1:1 reaction of a compound similar to the compound of general formula (II), in which, any other substitution and the reaction conditions remaining as described for the compound of general formula (II), the substituent A comprises 0 or 1 enantiopure amino acid.

The products obtained at the end of the method according to the invention can be derivatized, for example with known activating or protective groups. They can also be subjected to derivatization reactions aimed at introducing such activating or protective groups. The products obtained at the end of the method according to the invention, or their derivatives, can be used for the subsequent production of peptides or peptide derivatives, for example by known peptide couplings.

In a particular aspect, the method according to the invention also comprises the production of the compound of general formula (II) by peptide coupling of a fragment of general formula

XCH$_2$—C(=O)—HN—B  (VI)

in which X denotes a group which can be substituted by nucleophilic substitution, as defined above, chosen in particular from Cl and Br, and B denotes an amino acid or a peptide chain optionally bearing protective and/or activating groups, with a fragment F also denoting an amino acid or a peptide chain optionally bearing protective and/or activating groups.

In the fragment of general formula (VI), B can denote an amino acid, in particular chosen from glycine and the amino acids mentioned above. Preferably, B is an enantiopure amino acid, in particular as mentioned above, or a peptide in which the acylated N-terminus is an enantiopure amino acid. An enantiopure amino acid chosen from Phe, Ile, Val, Ala and Leu is particularly preferred. Phe is most particularly preferred as enantiopure amino acid.

Fragment F can be an amino acid or a peptide chain preferably comprising 2, 3, 4 or 5 amino acids. The amino acids are chosen in particular from glycine and the amino acids mentioned above.

Fragments B and F can bear protective and/or activating groups which are known in themselves, such as in particular a benzyloxycarbonyl group, a tert-butoxycarbonyl group or a silyl group. Fragments B and F can be coupled by known methods, such as, for example, a reaction of fragments of general formula (VI) and F, suitably protected in the presence of dicyclohexylcarbodiimide, optionally also in the presence of hydroxysuccinimide or of hydroxybenzotriazole.

It has been found that, despite the presence of acylated enantiopure amino acids or of enantiopure amino acids within a peptide chain in which the N-terminus is acylated, it is possible to perform multiple peptide couplings with a good yield of compound of general formula (II) while at the same time conserving a high optical purity.

In fragment F, the C-terminus is preferably a group —COOZ, the group Z of which can be substituted with a group Y as defined above, under conditions which leave the peptide bond intact and do not produce racemization. Examples of groups Z which can be used are silyl, in particular trialkylsilyl, groups. A trimethylsilyl group is particularly preferred as substituent Z In a particularly preferred variant, fragment F is persilylated, i.e. at least all the groups —$NH_2$ and COOH of the amino acid or of the peptide bear a silyl substituent, preferably a trialkylsilyl substituent (-$NJHSiR_3$; $COOSiR_3$). Trimethylsilyl groups are particularly preferred as silyl substituent. The persilylation of an amino acid or of a peptide can be carried out, for example, according to the method described in Patent Application EP-A-184243 in the Applicant's name.

In a most particularly preferred variant, fragment F is a persilylated amino acid. This fragment can be coupled with a fragment of general formula (VI) comprising a carboxyl group, which is preferably activated, for example by formation of acid chloride or anhydride.

The performing of successive peptide couplings of a fragment of general formula (VI), in which B denotes an amino acid as described above, with various fragments F which are persilylated, in particular pertrimethylsilylated, amino acids, is even more particularly preferred. This variant is particularly suitable for synthesizing compounds of general formula (III) in which A is a peptide chain consisting of a number greater than or equal to 2, 3, 4, 5, 6, 7 or 8 amino acids. This variant is particularly suitable for synthesizing compounds of general formula (II) in which A is a peptide chain consisting of a number less than or equal to 20, 15 or 10 amino acids. It has been found that the compounds of general formula (II) mentioned above in particular can be obtained economically on a preparative scale of hundreds of grams, or even of kilograms, with a high yield, with this variant, without substantial racemization.

The method according to the invention is particularly suitable for preparing N-Gly-terminal tetra-, penta-, hexa-, hepta- and octapeptides, such as in particular the sequences mentioned above, and more particularly Gly-Phe-Leu-Gly (SEQ ID NO: 1), by a sequence of reactions according to which (a) the synthesis of a compound of general formula (IJ) is carried out by successive peptide couplings of a fragment of general formula (VI) in which B denotes an amino acid as described above, in particular Ph; with various fragments F which are persilylated, in particular pertrimethylsilylated, amino acids;

(b) the compound of general formula (II) is subjected, in accordance with the method according to the invention as described above, to a reaction with a compound of general formula (III).

The examples below are intended to illustrate the invention without, however, limiting it.

The various products and synthetic intermediates reported in the examples were characterized by various analytical methods, used under the following conditions:

Optical rotation (α): measured at 589 nm at 25° C.
Thin layer chromatography (TLC):
MERCK 60F-254 silica gel plates
Eluents for the TLC
$R_f 1$: EtOAc/nBuOH/HOAc/$H_2O$ proportions (volume) 10/1/1/1
$R_f 2$: EtOAc/nBuOH/HOAc/$H_2O$ proportions (volume) 4/1/1/1
$R_f 3$: EtOAc/nBuOH/HOAc/$H_2O$ proportions (volume) 1/1/1/1
HPLC chromatography:
Vydac 5 μm 201 TP 54 C-18 column
Elution: gradient from 98% A+2% B up to 25% A+75% B in 49 minutes
(A=0.1% water in trifluoroacetic acid; B=0.1% acetonitrile in trifluoroacetic acid)
Flow rate=2 ml/min
Detection: UV 220 nm.
Nuclear magnetic resonance (NMR):
Brüker AMX 500 MHz device
Shift given in ppm
Appearance of resonances: m=multiplet, s=singlet, d=doublet, t=triplet, q=quadruplet, quint=quintuplet, o=octuplet.

EXAMPLE 1

Synthesis of N-chloroacetyl-Phe-Leu
Activation
A solution of 1 mol of N-chloroacetyl-(L)-phenylalanine in 1 litre of dichloromethane in the presence of one mole of triethylamine and of 1 mol of pyridine was prepared. The solution was cooled to −35° C. and 1.15 mol of pivaloyl chloride were added.

Coupling 1 litre of a solution of 1.15 mol of N,O-bis(trimethylsilyl)-(L)-leucine in dichloromethane, cooled to −15° C., was added to the prepared solution. The mixture was allowed to react for 90 min while allowing the temperature to come back up.

Isolation of the Compound

The reaction mixture was treated with a solution of 1 mol of $KHSO_4$ in 2.7 litres of water. The dichloromethane was evaporated off and the N-chloroacetyl-Phe-Leu was recovered in the form of a precipitate, which was dried and washed with ether.
Yield 80%
No racemization was observed.

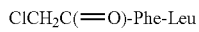

m.p.: 158-159° C.
α: −10:2 (C=2, $CH_3OH$)
TLC: $R_f 1$: 0.86
HPLC: $t_R$: 19.8 min ($^1$H) NMR in CD$_3$OD, internal reference (central line of the CD$_3$ multiplet at 3.32 ppm)

| | | |
|---|---|---|
| 7.26-7.21 | (5H, m) | aromatic Hs Phe |
| 4.72 | (1H, dd) | Hα Phe |
| 4.46 | (1H, dd) | Hα Leu |
| 4.00 | (2H, system AB) | ClCH$_2$—C(=O) |
| 3.20 | (1H, dd) | H$_\beta$1 Phe |
| 2.94 | (1H, dd) | H$_\beta$2 Phe |
| 1.71 | (1H, m) | H$_\gamma$ Leu |
| 1.67 | (1H, m) | H$_\beta$ Leu |
| 0.96 | (3H, d) | CH$_3$ γ1 Leu |
| 0.95 | (3H, d) | CH$_3$ γ2 Leu |

EXAMPLE 2

Synthesis of N-chloroacetyl-Phe-Leu-Gly

The procedure as in Example 1 was carried out, with the following differences:

N-Chloroacetyl-Phe-Leu was used in the activation step and N,O-bis(trimethylsilyl)glycine was used in the coupling step.

Yield 75%

No racemization was observed.

ClCH$_2$CO-Phe-Leu-Gly m.p.: 207-209° C.

α: −31 (C=2, CH$_3$OH)

TLC: R$_1$(1): 0.67

HPLC: t$_R$: 17.2 min ($^1$H) NMR in CD$_3$ OD, internal reference (central line of the CD$_3$ multiplet at 3.32 ppm)

| | | |
|---|---|---|
| 7.28-7.22 | (5H, m) | aromatic Hs Phe |
| 4.96 | (1H, dd) | Hα Phe |
| 4.47 | (1H, dd) | Hα Leu |
| 4.01 | (2H, system AB) | ClCH$_2$—C(=O) |
| 3.87 | (2H, system AB) | Hα-Gly |
| 3.17 | (1H, dd) | H$_\beta$1 Phe |
| 2.98 | (1H, dd) | H$_\beta$2 Phe |
| 1.65 | (3H, m) | H$_\beta$ + H$_\gamma$ Leu |
| 0.95 | (3H, d) | CH$_3$ γ1 Leu |
| 0.94 | (3H, d) | CH$_3$ γ2 Leu |

EXAMPLE 3

Synthesis of Gly-Phe-Leu-Gly (SEQ ID NO: 1)

3 portions of 10 g of N-chloroacetyl-Phe-Leu-Gly, at ambient temperature, were introduced into 1 l of aqueous ammonia (25%). The time between the introductions of N-chloroacetyl-Phe-Leu-Gly was 6 h each time. After a further 6 h, the aqueous ammonia was evaporated off until the product precipitated.

The mother liquors were neutralized and stored at −5° C. The product was filtered and washed with water.

Yield of Gly-Phe-Leu-Gly: 80%

Gly-Phe-Leu-Gly m.p.: (decomposition)>300° C.

α: −26 (C=2, 1N HCl)

TLC: R$_f$(1)=0.12

R$_f$(3)=0.25

R$_f$(3)=0.51

HPLC: t$_R$: 11.6 min ($^1$H) NMR in CD$_3$OD, internal reference (central line of the CD$_3$ multiplet at 3.32 ppm)

| | | |
|---|---|---|
| 7.27-7.22 | (5H, m) | aromatic Hs Phe |
| 4.72 | (1H, dd) | Hα Phe |
| 4.46 | (1H, dd) | Hα Leu |
| 3.91 | (2H, system AB) | Hα Gly 2 |
| 3.70 | (1H, d) | Hα1 Gly 1 |
| 3.62 | (1H, d) | Hα2 Gly 1 |
| 3.17 | (1H, dd) | H$_\beta$1 Phe |
| 2.93 | (1H, dd) | H$_\beta$2 Phe |
| 1.63 | (3H, m) | H$_\beta$ + H$_\gamma$ Leu |
| 0.95 | (3H, d) | CH$_3$ γ1 Leu |
| 0.94 | (3H, d) | CH$_3$ γ2 Leu |

The product HN(CH$_2$(C=O)-Phe-Leu-Gly)$_2$ was obtained by acidification of the mother liquors, with a yield of 5%.

No racemization was observed for the two products.

EXAMPLE 4

Synthesis of 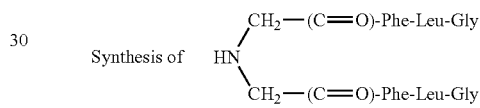

1.25 mmol (490 mg) of Gly-Phe-Leu-Gly and 1 mmol (411 mg) of ClCH$_2$(C=O)-Phe-Leu-Gly were dissolved in 5 ml of dioxane and 2.25 ml of 1N KOH. The mixture was heated to approximately 65° C. and the conversion was followed by HPLC. As soon as the conversion was complete, the dioxane was evaporated off. 10 ml of water were added and the pH was adjusted to 2.5. The product was precipitated. It was washed with water and with ethyl acetate.

Yield: 60% t$_R$(HPLC):21.0 min

R$_f$2=0.75

NMR (D$_2$O+1 drop of trifluoroacetic acid)

| | | |
|---|---|---|
| 7.45-7.36 | (m, 10H) | aromatic Hs Phe |
| 4.84 | (m, 2H) | Hα of two Phe |
| 4.59 | (m, 2H) | Hα of two Leu |
| 4.14-4.00 | (m, 8H) | Hα of Gly groups |
| 3.23 | (m, 4H) | Hβ of two Phe |
| 1.70 | (m, 6H) | Hβ + Hγ of two Leu |
| 1.00 | (d + d, 12H) | Hδ of two Leu |

EXAMPLE 5

Synthesis of 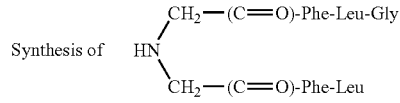

The compound was obtained by following the procedure of Example 4, starting with Gly-Phe-Leu-Gly and ClCH$_2$(C=O)-Phe-Leu.

$t_R$=22.4min
$R_f2$: 0.84
($^1$H) NMR in CD$_3$OD, internal reference (central line of the CD$_3$ multiplet at 3.32 ppm)

| | | |
|---|---|---|
| 7.30-7.23 | (m, 10H) | aromatic Hs Phe |
| 4.73 | (dd, 1H) | Hα of the 1st Phe |
| 4.67 | (dd, 2H) | Hα of the 2nd Phe |
| 3.88 | (s, 2H) | Hα of a Gly group |
| 3.55 | (system AB, 4H) | Hα of two Gly |
| 3.32 | (m, 2H) | Hβ1 of two Phe |
| 3.23 | (m, 2H) | Hβ2 of two Phe |
| 1.75-1.68 | (m, 6H) | Hβ + Hγ of two Leu |
| 0.98-0.95 | (m, 12H) | Hδ of two Leu |

---

The invention claimed is:

1. A method for preparing a peptide of general formula $$R^1R^2NCH_2-C(=O)-HN-A-COOH \quad (I)$$

in which A is a peptide chain comprising at least two enantiopure amino acids; and $R^1$ and $R^2$ are each H, HN represents the terminal amino group of A and COOH represents the terminal carboxyl group of A, comprising a) producing a compound of general formula $$XCH_2-C(=O)-HN-A-COOY \quad (II);$$

wherein

X is a group which can be substituted by nucleophilic substitution, chosen from Cl and Br;

Y is selected from the group consisting of H, $Li^+$, $Na^+$, $K^+$, $Cs^+$, $Mg^{2+}$, $Ca^{2+}$, $Sr^{2+}$, and $Ba^{2+}$;

A has the same meaning as in formula (I);

HN represents the terminal amino group of A; and

COOY represents the terminal carboxyl group of A, by peptide coupling of a fragment of general formula $$XCH_2-C(=O)-HN-B \quad (VI)$$

wherein

X is a group which can be substituted by nucleophilic substitution, chosen from Cl and Br, B is an amino acid or a peptide chain optionally bearing protective and/or activating groups, HN represents the α- amino group when B is an amino acid or the terminal amino group of B when B is a peptide, with a fragment F, wherein fragment F is a persilylated amino acid or a persilylated peptide chain;

and b) reacting said compound of general formula (II) as defined in a) with a compound of general formula $HNR^1R^2$ (III) in which $R^1$ and $R^2$ are each H, wherein the reaction is carried out at a temperature of −30° C. to +60° C.

2. The method according to claim 1, in which the reaction is carried out at a temperature of 0° C. to +50° C.

3. The method according to claim 1, in which the reaction is carried out at a temperature of +10° C. to +40° C.

4. The method according to claim 1, in which the reaction is carried out in a liquid medium containing at least 25% by weight, relative to the total weight of the liquid medium, of compound of general formula (III).

5. The method according to claim 4, in which the liquid medium contains at least 30% by weight of compound of general formula (III).

6. The method according to claim 1, in which the reaction is carried out in a liquid medium in which a concentration of the compound of general formula (II) of less than or equal to 10% by weight relative to the total weight of the liquid medium, is maintained.

7. The method according to claim 1, in which the compound of general formula (III) is aqueous ammonia.

8. The method according to claim 1, in which A is a peptide chain made up of 2 to 20 amino acids.

9. The method according to claim 1, in which B is an amino acid.

10. The method according to claim 1, in which the group A of the compound of general formula (II) is Phe-Leu-Gly.

11. The method according to claim 4, in which the group A of the compound of general formula (II) is Phe-Leu-Gly.

12. The method according to claim 5, in which the group A of the compound of general formula (II) is Phe-Leu-Gly.

13. The method according to claim 6, in which the group A of the compound of general formula (II) is Phe-Leu-Gly.

14. The method according to claim 7, in which the group A of the compound of general formula (II) is Phe-Leu-Gly.

15. The method according to claim 8, in which the group A of the compound of general formula (II) is Phe-Leu-Gly.

16. The method according to claim 9, in which the group A of the compound of general formula (II) is Phe-Leu-Gly.

* * * * *

SEQUENCE LISTING

<160> NUMBER OF SEQ ID NOS: 5

<210> SEQ ID NO 1
<211> LENGTH: 4
<212> TYPE: PRT
<213> ORGANISM: Artificial
<220> FEATURE:
<223> OTHER INFORMATION: Synthetic peptide

<400> SEQUENCE: 1

Gly Phe Leu Gly
1

<210> SEQ ID NO 2
<211> LENGTH: 4
<212> TYPE: PRT
<213> ORGANISM: Artificial
<220> FEATURE:
<223> OTHER INFORMATION: Synthetic peptide

<400> SEQUENCE: 2

Gly Phe Gly Phe
1

<210> SEQ ID NO 3
<211> LENGTH: 4
<212> TYPE: PRT
<213> ORGANISM: Artificial
<220> FEATURE:
<223> OTHER INFORMATION: Synthetic peptide

<400> SEQUENCE: 3

Gly Phe Gly Leu
1

<210> SEQ ID NO 4
<211> LENGTH: 5
<212> TYPE: PRT
<213> ORGANISM: Artificial
<220> FEATURE:
<223> OTHER INFORMATION: Synthetic peptide

<400> SEQUENCE: 4

Gly Phe Gly Phe Leu
1               5

<210> SEQ ID NO 5
<211> LENGTH: 6
<212> TYPE: PRT
<213> ORGANISM: Artificial
<220> FEATURE:
<223> OTHER INFORMATION: Synthetic peptide

```
<400> SEQUENCE: 5

Gly Phe Leu Gly Phe Leu
1               5
```